US012582559B2

(12) United States Patent
Young et al.

(10) Patent No.: US 12,582,559 B2
(45) Date of Patent: Mar. 24, 2026

(54) BI-DIRECTIONALLY POSITIONABLE TAMPON

(71) Applicant: Outasite, LLC, Cary, NC (US)

(72) Inventors: Terrill A. Young, Cincinnati, OH (US); Gwynne Marie Hite, Morrisville, NC (US); Walter Dan Parker, Tucson, AZ (US)

(73) Assignee: Outasite, LLC, Cary, NC (US)

( * ) Notice: Subject to any disclaimer, the term of this patent is extended or adjusted under 35 U.S.C. 154(b) by 414 days.

(21) Appl. No.: 17/702,870

(22) Filed: Mar. 24, 2022

(65) Prior Publication Data

US 2023/0301842 A1 Sep. 28, 2023

(51) Int. Cl.
*A61F 13/20* (2006.01)
(52) U.S. Cl.
CPC ...... *A61F 13/2042* (2013.01); *A61F 13/2071* (2013.01)
(58) Field of Classification Search
CPC .............. A61F 13/2045; A61F 13/2042; A61F 5/4553; A61F 2013/47281; A61F 6/08; A61F 13/20
See application file for complete search history.

(56) References Cited

U.S. PATENT DOCUMENTS

| | | | |
|---|---|---|---|
| 2,309,868 A | 2/1943 | Robertson | |
| 3,128,767 A | 4/1964 | Nolan | |
| 3,216,422 A | * 11/1965 | Steiger | A61F 6/08 604/330 |
| 3,658,057 A | 4/1972 | Climber | |
| 3,983,874 A | 10/1976 | Davis et al. | |

(Continued)

FOREIGN PATENT DOCUMENTS

| | | | |
|---|---|---|---|
| CA | 2137769 A1 | 5/1996 | |
| CA | 2285989 A1 | * 10/1998 | |

(Continued)

OTHER PUBLICATIONS

Non-Final Office Action for U.S. Appl. No. 17/752,255, mailed Jul. 18, 2023, 7 pages.

(Continued)

*Primary Examiner* — Philip R Wiest
*Assistant Examiner* — Linnae E. Raymond
(74) *Attorney, Agent, or Firm* — Withrow + Terranova, PLLC; Vincent K. Gustafson

(57) ABSTRACT

Bi-directionally positionable tampon configured to be disposed in a vaginal opening adjacent to a cervical os for absorbing and collecting vaginal discharge. The tampon includes an elastomeric ring to support an absorbent pad for collecting and absorbing bodily fluids. To support the absorbent pad, the elastomeric ring has a first circular-shaped edge and a second circular-shaped edge that surrounds the central aperture. A covering comprising a first pervious layer and a second pervious layer disposed adjacent to the first pervious layer is attached to the elastomeric ring and disposed at least partially in the central aperture of the ring. An absorbent pad is disposed in a cavity formed between the first fabric layer and the second fabric layer of the covering. When the elastomeric ring is disposed in a vaginal opening, bodily fluid can pass through either the first and/or second pervious layers to reach the absorbent pad.

25 Claims, 8 Drawing Sheets

(56) References Cited

U.S. PATENT DOCUMENTS

| 4,198,976 | A | 4/1980 | Drobish et al. |
|---|---|---|---|
| 4,200,090 | A | 4/1980 | Drobish |
| 4,219,016 | A | 8/1980 | Drobish et al. |
| 4,304,226 | A | 12/1981 | Drobish et al. |
| 4,320,751 | A | 3/1982 | Loeb |
| 4,322,463 | A | 3/1982 | Goepp et al. |
| 4,326,510 | A | 4/1982 | Buckles |
| 4,363,318 | A | 12/1982 | Goepp et al. |
| 4,369,219 | A | 1/1983 | Goepp et al. |
| 4,369,773 | A | 1/1983 | Chvapil |
| 4,381,771 | A | 5/1983 | Gabbay |
| 4,384,572 | A | 5/1983 | Goepp |
| 4,393,871 | A | 7/1983 | Vorhauer et al. |
| 4,401,534 | A | 8/1983 | Goepp et al. |
| 4,450,836 | A | 5/1984 | Goepp et al. |
| 4,467,789 | A | 8/1984 | Goepp et al. |
| 4,517,970 | A | 5/1985 | Goepp et al. |
| 4,543,949 | A | 10/1985 | Goepp et al. |
| 4,589,880 | A | 5/1986 | Dunn et al. |
| 4,703,752 | A | 11/1987 | Gabbay |
| 4,848,363 | A | 7/1989 | Cattanach |
| 4,858,624 | A | 8/1989 | Shihata |
| 4,959,216 | A | 9/1990 | Daunter |
| 4,989,618 | A | 2/1991 | Shihata |
| 5,000,749 | A | 3/1991 | LeVeen et al. |
| 5,070,889 | A | 12/1991 | Leveen et al. |
| 5,156,164 | A | 10/1992 | LeVeen et al. |
| 5,207,232 | A | 5/1993 | Shihata |
| 5,231,992 | A | 8/1993 | Leon |
| 5,295,984 | A | 3/1994 | Contente et al. |
| 5,527,534 | A | 6/1996 | Myhling |
| 5,592,949 | A | 1/1997 | Moench et al. |
| 5,617,877 | A | 4/1997 | Moench et al. |
| 5,771,900 | A | 6/1998 | Austin et al. |
| 5,928,184 | A | 7/1999 | Etheredge et al. |
| 6,126,616 | A | 10/2000 | Sanyal |
| 6,177,606 | B1 | 1/2001 | Etheredge et al. |
| 6,264,638 | B1 * | 7/2001 | Contente ............ A61M 31/002 |
| | | | 604/285 |
| 6,332,878 | B1 | 12/2001 | Wray et al. |
| 6,796,973 | B1 | 9/2004 | Contente et al. |
| 7,192,630 | B2 | 3/2007 | Ziltener et al. |
| 10,226,387 | B2 | 3/2019 | Hite |
| 10,383,775 | B2 | 8/2019 | Edmunds |
| 11,389,338 | B2 | 7/2022 | Hite |
| 2007/0289598 | A1 | 12/2007 | LaBarre et al. |
| 2008/0200888 | A1 | 8/2008 | Gooch et al. |
| 2016/0081860 | A1 | 3/2016 | Hite |
| 2016/0278988 | A1 | 9/2016 | Knox |
| 2017/0198432 | A1 * | 7/2017 | Richards ................ D06N 3/125 |
| 2019/0201248 | A1 * | 7/2019 | Hite .................... A61F 13/2045 |
| 2021/0128342 | A1 * | 5/2021 | Miller ..................... A61F 5/455 |
| 2021/0378880 | A1 * | 12/2021 | Nur ......................... A61L 15/18 |

FOREIGN PATENT DOCUMENTS

| EP | 0134671 | A1 | 4/1987 | | |
|---|---|---|---|---|---|
| WO | 8701581 | A1 | 3/1987 | | |
| WO | 9108779 | A1 | 6/1991 | | |
| WO | 9400168 | A1 | 1/1994 | | |
| WO | WO-9814145 | A1 * | 4/1998 | .............. | A61F 5/44 |
| WO | 9843687 | A1 | 10/1998 | | |
| WO | 0115757 | A1 | 8/2001 | | |
| WO | WO-03051257 | A1 * | 6/2003 | ......... | A61F 13/2051 |
| WO | WO-2007147116 | A2 * | 12/2007 | ............. | A61F 13/20 |
| WO | WO-2017205356 | A1 * | 11/2017 | ......... | A61F 13/2028 |
| WO | WO-2020089980 | A1 * | 5/2020 | | |

OTHER PUBLICATIONS

Author Unknown, "Reusable Resolutions & Resuable Instead Softcup," The Vagina Monologues, Dec. 26, 2011, vagmonologues.blogspot. com/2011/12/reusable-resolutions-reusable-instead.html, 13 pages.

Beppy, "Beppy Soft + Comfort TamponsDry envelope (4pcs)," accessed Oct. 4, 2021 from https://www.beppy.com/en/product/beppy-soft-comfort-tampons-dry-envelope-4pcs/, 2 pages.

Beppy, "Beppy Soft + Comfort TamponsWet envelope (4pcs)," accessed Oct. 4, 2021 from https://www.beppy.com/en/product/beppy-soft-comfort-tampons-wet-envelope-4pcs/, 2 pages.

Beppy, "Feel Free, Do What You Like, Every Day of the Month!" available as early as Dec. 2019 from https://www.beppy.com/en/home/, 4 pages.

Cattanach, J., "The Gynaeseal diaphragm tampon," The Medical Journal of Australia, vol. 152, Issue 1, Jan. 1990, 2 pages.

Diva International Inc., "Goodbye Tampons," available as early as Dec. 2019 from https://divacup.com/, 7 pages.

The Flex Company, "Shop Flex Disc | Flex® Sustainable Period Products," available as early as Dec. 2019 from https://flexfits.com/, 6 pages.

Joydivision, "Discover stringless Soft-Tampons by Joydivision," available as early as Dec. 2019 from https://joydivision.de/en/all-products/soft-tampons-professional-box-of-50, 4 pages.

North, B. et al., "Preclinical, Clinical, and Over-the-Counter Postmarketing Experience with a New Vaginal Cup: Menstrual Collection," Journal of Women's Health, vol. 20, No. 2, Feb. 13, 2011, 18 pages.

Sree, "Recent interventions in barrier contraceptive methods," Obs &Gyn, Nov. 22, 2013, srsree.blogspot.com/2013/11/recent-interventions-in-barrier.html, 6 pages.

Williams, L., "What is a Softcup?" Apr. 12, 2012, SheKnows, https://www.sheknows.com/health-and-wellness/articles/953517/what-is-a-softcup/, 11 pages.

Non-Final Office Action for U.S. Appl. No. 14/860,073, mailed Dec. 29, 2017, 10 pages.

Applicant-Initiated Interview Summary for U.S. Appl. No. 14/860,073, mailed Jul. 3, 2018, 3 pages.

Notice of Allowance for U.S. Appl. No. 14/860,073, mailed Oct. 29, 2018, 8 pages.

Corrected Notice of Allowability for U.S. Appl. No. 14/860,073, mailed Dec. 3, 2018, 4 pages.

Issue Notification for U.S. Appl. No. 14/860,073, mailed Feb. 20, 2019, 1 page.

Non-Final Office Action for U.S. Appl. No. 16/299,791, mailed Aug. 30, 2021, 11 pages.

Notice of Allowance for U.S. Appl. No. 16/299,791, mailed Apr. 1, 2022, 8 pages.

Notice of Allowance for U.S. Appl. No. 17/752,255, mailed Oct. 30, 2023, 8 pages.

* cited by examiner

CERVICAL PAD
100

CERVICAL PAD
100

CIRCULAR PAD
100

106

108

$D_1$

Z
Y
X

CIRCULAR PAD
100

106

$D_4$

108

106

Z
Y
X

BI-DIRECTIONALLY POSITIONABLE TAMPON

FIELD OF THE DISCLOSURE

The field of the disclosure relates to a feminine hygiene device, and more particularly to an intravaginal device comprising a tampon for absorbing and collecting bodily fluids and other vaginal discharge.

BACKGROUND

Cervical pads, such as menstrual napkins and tampons, are feminine products that are used to absorb blood, vaginal discharge, and other bodily fluids. Conventional cervical pads, including menstrual napkins, tampons, and non-absorbent collection reservoirs often leak during active use. Further, conventional cervical pads are designed so that they cannot be used during sexual intercourse or other sexual contact.

SUMMARY OF THE DISCLOSURE

Aspects disclosed herein include a bi-directionally positionable tampon that is configured to be disposed in a vaginal opening adjacent to a cervical os for absorbing and collecting vaginal discharge and other body fluids, particularly during menses. In this regard, the tampon is also referred to as "cervical pad." In exemplary aspects, the tampon includes an elastomeric ring that defines a central aperture to support an absorbent pad for collecting and absorbing bodily fluids. The elastomeric ring is substantially reduced in width versus in diameter or length to be substantially flat or "horizontal" for convenient insertion and placement adjacent to a cervical os. The ring being elastomeric allows the tampon to be deformed under force for easy insertion into a vaginal opening and then reformed after force is released to its original or substantially original shape within the vaginal canal. To support the absorbent pad, the elastomeric ring has a first circular-shaped edge and a second circular-shaped edge that surrounds the central aperture, wherein the second circular edge is opposite from the first circular-shaped edge. A covering comprising a first pervious layer (e.g., a first fabric layer) and a second pervious layer (e.g., a second fabric layer) disposed adjacent to the first pervious layer are attached to the elastomeric ring and disposed at least partially in the central aperture of the ring. An absorbent pad is disposed in a cavity formed between the first fabric layer and the second fabric layer of the covering to position the absorbent pad within the central aperture of the elastomeric ring. In this manner, when the elastomeric ring is disposed in a vaginal opening, bodily fluid can pass through the first and/or second pervious layers of its covering to reach the absorbent pad disposed therein to be collected and absorbed.

The first and second pervious layers of the covering both being pervious allows the tampon to be positioned in the vaginal opening symmetrically and bi-directionally with either of the first or second pervious layer disposed adjacent to the cervical os. This is because in either position of first or second pervious layer of the covering disposed adjacent to the cervical os, bodily fluid can pass through the first or second pervious layer to reach the absorbent pad. This allows for an easier use of the tampon. For example, if only one of the layers of the covering were pervious, a user would have to understand which side of the covering is pervious and then orient the tampon with the pervious side to be positioned adjacent to the cervical os. In the exemplary tampons disclosed herein, the user does not have to understand which side of the tampon has the pervious layer. The user can position the tampon in the vaginal canal with either side positioned adjacent to the cervical os.

In other exemplary aspects, to further support the tampon being bi-directionally positionable within the vaginal canal, the covering of the tampon is at least partially positioned between the first circular-shaped edge and the second circular-shaped edge of the elastomeric ring. In this manner, at least portions of the first and second circular-shaped edges of the elastomeric ring will extend beyond outer surfaces of the first and second pervious layers of the covering to form collection chambers on each side of the elastomeric ring. The collection chambers are bounded by an inner surface (e.g., inner wall) of the elastomeric ring that extends beyond outer surfaces of the first and second pervious layers. This may further aid in collection of bodily fluids within the central aperture area of the elastomeric ring that will then pass through a pervious layer of the covering to reach the absorbent pad.

In yet other exemplary aspects, to prevent or reduce the tearing or compromising of the structural integrity of the absorbent pad when the elastomeric ring is deformed to insert the tampon into a vaginal opening, the absorbent pad is floatingly disposed in the cavity between the first and second pervious layers of the covering. In this manner, when the elastomeric ring is deformed for insertion of the tampon into a vaginal opening, the force applied to the elastomeric ring is not directly translated to the absorbent pad. Force applied to the elastomeric ring may be translated to the first and second pervious layers of the covering, but the first and second pervious layers are chosen from material(s) that allow the first and second pervious layers to stretch with no or lower risk of tearing. This allows an absorbent pad for the tampon to be chosen from a material that is based on the desired collection and absorption properties without such properties having to be compromised to avoid or reduce tearing as if the absorbent pad were fixedly attached to the elastomeric ring.

In this regard, in one exemplary aspect, a tampon is provided. The tampon comprises an elastomeric ring defining a central aperture. The elastomeric ring comprises a first circular-shaped edge and a second circular-shaped edge opposite the first circular-shaped edge. The tampon also comprises a covering attached to the elastomeric ring. The covering is at least partially positioned within the central aperture and at least partially positioned between the first circular-shaped edge and the second circular-shaped edge, the covering comprising a first pervious layer and a second pervious layer at least partially defining a cavity therebetween, the first pervious layer and the second pervious layer being of a substantially same surface area. An absorbent pad is floatingly positioned within the cavity and substantially centered between the first circular-shaped edge and the second circular-shaped edge of the elastomeric ring.

DETAILED DESCRIPTION

Figure 1:
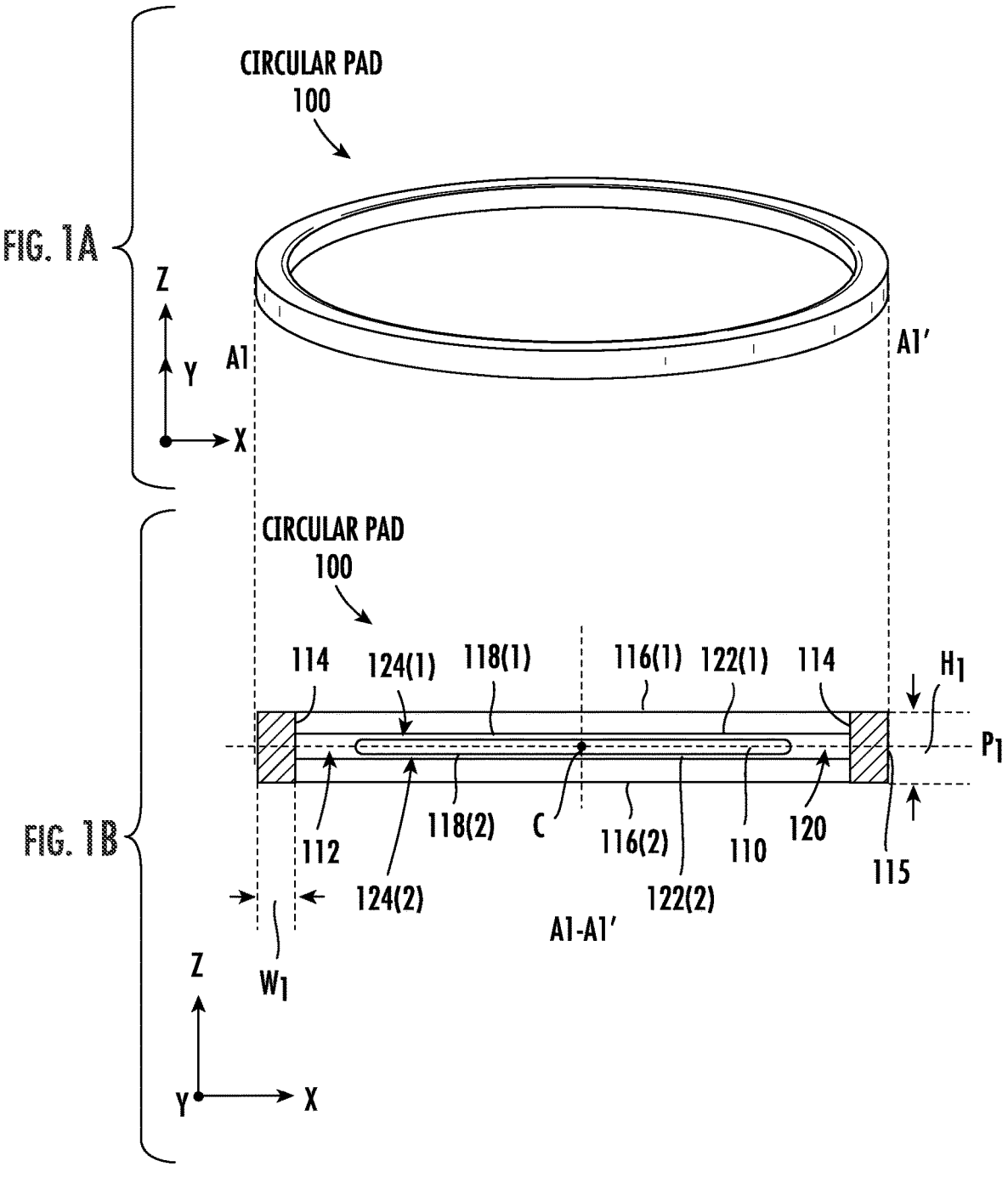
FIGS. 1A and 1B are top perspective and side cross-sectional views, respectively, of an exemplary bi-directionally positionable tampon that has an absorbent pad disposed in a cavity formed between adjacent pervious fabric layers of a covering attached to an elastomeric ring.

With reference now to the drawing figures, several exemplary aspects of the present disclosure are described. The word "exemplary" is used herein to mean "serving as an example, instance, or illustration." Any aspect described herein as "exemplary" is not necessarily to be construed as preferred or advantageous over other aspects.

Aspects disclosed herein include a bi-directionally positionable tampon that is configured to be disposed in a vaginal opening adjacent to a cervical os for absorbing and collecting vaginal discharge and other body fluids, particularly during menses. In exemplary aspects, the tampon includes an elastomeric ring that defines a central aperture to support an absorbent pad for collecting and absorbing bodily fluids. The elastomeric ring is substantially reduced in width versus in diameter or length to be substantially flat or "horizontal" for convenient insertion and placement adjacent to a cervical os. The ring being elastomeric allows the tampon to be deformed under force for easy insertion into a vaginal opening and then reformed after force is released to its original or substantially original shape within the vaginal canal. To support the absorbent pad, the elastomeric ring has a first circular-shaped edge and a second circular-shaped edge that surrounds the central aperture, wherein the second circular edge is opposite from the first circular-shaped edge. A covering comprising a first pervious layer (e.g., a first fabric layer) and a second pervious layer (e.g., a second fabric layer) disposed adjacent to the first pervious layer are attached to the elastomeric ring and disposed at least partially in the central aperture of the ring. An absorbent pad is disposed in a cavity formed between the first fabric layer and the second fabric layer of the covering to position the absorbent pad within the central aperture of the elastomeric ring. In this manner, when the elastomeric ring is disposed in a vaginal opening, bodily fluid can pass through the first and/or second pervious layers of its covering to reach the absorbent pad disposed therein to be collected and absorbed.

The first and second pervious layers of the covering both being pervious allows the tampon to be positioned in the vaginal opening bi-directionally and symmetrically with either of the first or second pervious layer disposed adjacent to the cervical os. This is because in either position of first or second pervious layer of the covering disposed adjacent to the cervical os, bodily fluid can pass through the first or second pervious layer to reach the absorbent pad. This allows for an easier use of the tampon. For example, if only one of the layers of the covering were pervious, a user would have to understand which side of the covering is pervious and then orient the tampon with the pervious side to be positioned adjacent to the cervical os. In the exemplary tampons disclosed herein, the user does not have to understand which side of the tampon has the pervious layer. The user can position the tampon in the vaginal canal with either side positioned adjacent to the cervical os.

Figure 2:
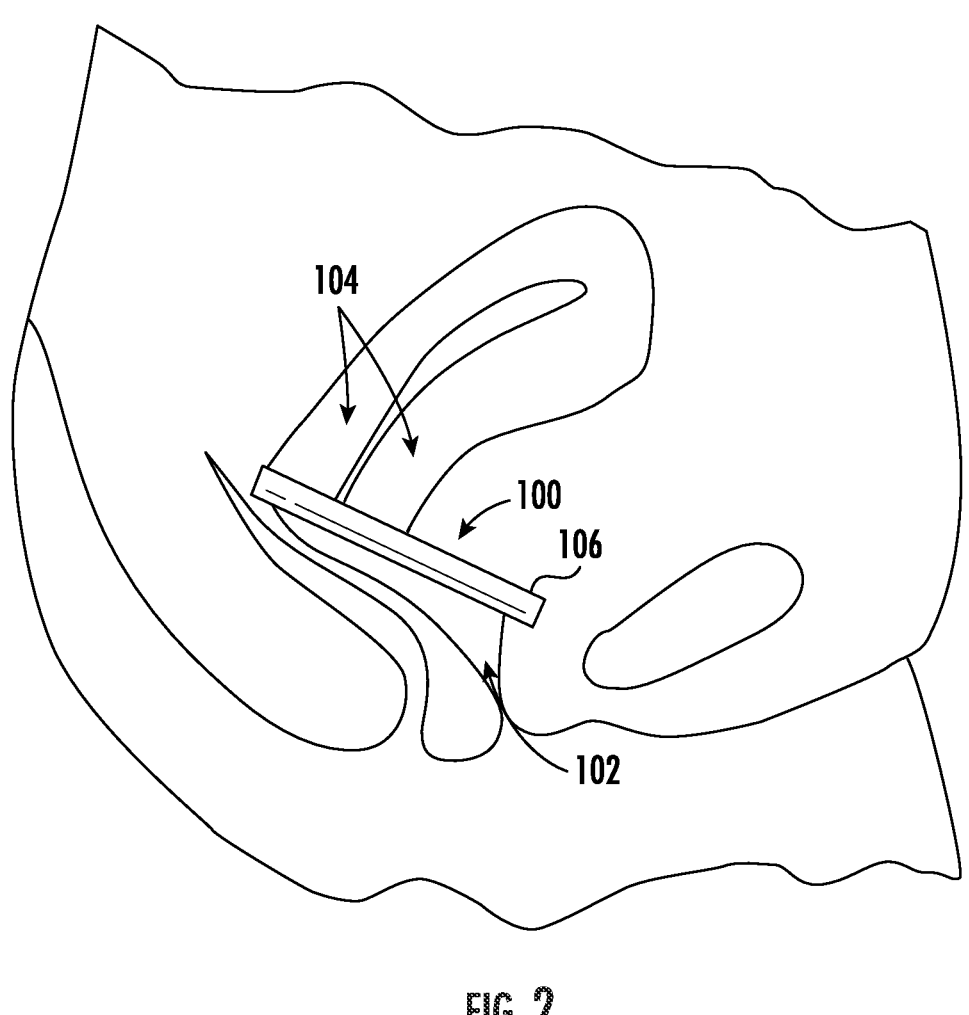
FIG. 2 is schematic diagram of a tampon positioned in a vaginal canal.

In this regard, FIGS. 1A and 1B are top perspective and side cross-sectional views, respectively, of an exemplary bi-directionally positionable tampon 100 (referred to herein as "tampon 100"). FIG. 1B is a side cross-sectional view of the tampon 100 in FIG. 1A along the A1-A1' line. As shown in FIG. 2, the tampon 100 is configured to be disposed in and span a vaginal opening 102 adjacent to a cervical os 104 for absorbing and collecting vaginal discharge and other body fluids, particularly during menses. With reference back to FIGS. 1A and 1B, as discussed in more detail below, the tampon 100 includes an elastomeric ring 106 that defines a central aperture 108 to support an absorbent pad 110 for collecting and absorbing bodily fluids. For example, the elastomeric ring 106 may be made out of silicone or other thermoplastic elastomers as non-limiting examples. The absorbent pad 110 is supported within the central aperture 108 of the elastomeric ring 106 such that manipulation of the elastomeric ring 106 can position the absorbent pad 110 in the desired location and orientation. As shown in the top and top perspective views, respectively, of the tampon 100 in FIGS. 3A and 3B, the elastomeric ring 106 being elastomeric allows the elastomeric ring 106 and tampon 100 to be deformed under force (shown by force arrows $F_1$, $F_2$ in the Y-axis direction in this example) for easy insertion into a vaginal opening. After the tampon is inserted into a vaginal opening and positioned as desired, the force applied to the elastomeric ring 106 can then be released so that the elastomeric ring 106 recovers to its original form and shape, as shown in top view of the tampon in FIG. 3C.

To support the absorbent pad 110 within the central aperture 108 of the elastomeric ring 106, a covering 112 is disposed in the central aperture 108. The covering 112 can be attached to an inner surface 114 of the elastomeric ring 106, for example. The inner surface 114 is located opposite of an outer surface 115 of the elastomeric ring 106, as shown in FIGS. 1A and 1B. The covering 112 can be attached to the inner surface 114 anywhere between a first circular-shaped edge 116(1) and a second circular-shaped edge 116(2) of the elastomeric ring 106, both of which surround the central aperture 108. If the covering 112 is attached approximately midway between the first and second circular-shaped edges 116(1), 116(2), this position could more easily enable a finger grasp of the elastomeric ring 106 from either side of the covering 112 when removing from the body. The second circular-shaped edge 116(2) is opposite from the first circular-shaped edge 116(1) in the Z-axis direction. In this example, the covering 112 includes a first pervious layer 118(1) (e.g., a first fabric layer) and a second pervious layer 118(2) (e.g., a second fabric layer) disposed adjacent to the first pervious layer 118(1), such that the covering 112 is at least partially disposed in the central aperture 108 of the elastomeric ring 106. For example, the covering 112 and its first and second pervious layers 118(1), 118(2) could be attached to the inner surface 114 of the elastomeric ring 106 midway between the first circular-shaped edge 116(1) and the second circular-shaped edge 116(2) in the Z-axis direction. As another example, the covering 112 and its first and second pervious layers 118(1), 118(2) could be attached (e.g., permanently attached) to the inner surface 114 of the elastomeric ring 106 midway at the first circular-shaped edge 116(1) and the second circular-shaped edge 116(2) in the Z-axis direction. The first and second pervious layers 118(1), 118(2) do not extend past the first and second-circular shaped edges 116(1), 116(2) in the Z-axis direction in this example.

By the first and second pervious layers 118(1), 118(2) being disposed adjacent to each other and attached to the elastomeric ring 106, a cavity 120 is formed between the first and second pervious layers 118(1), 118(2) as shown in FIG. 1B. The absorbent pad 110 is disposed in the cavity 120 sandwiched between the first and second pervious layers 118(1), 118(2) of the covering 112 to position and support the absorbent pad 110 being located within the central aperture 108 of the elastomeric ring 106. In this manner, when the elastomeric ring 106 is disposed in a vaginal opening, bodily fluid can pass through the first and/or second pervious layers 118(1), 118(2) of its covering 112 to reach the absorbent pad 110 disposed therein to be collected and absorbed. As an example, the first and second pervious layers 118(1), 118(2) and the absorbent pad 110 are generally planar structures so that the tampon 100 has a substantially flat dimension in the Z-axis direction as compared to the X- and Y-axis dimensions.

With continuing reference to the tampon 100 in FIGS. 1A and 1B, the first and second pervious layers 118(1), 118(2) of the covering 112 both being pervious in this example allows the tampon 100 to be positioned in the vaginal opening bi-directionally with either of the first or second pervious layer 118(1), 118(2) disposed adjacent to a cervical os. This is based on, in this example and as shown in FIG. 1B, the tampon 100 being symmetrical about a central plane $P_1$ perpendicular to a central axis $C_1$ defined by the elastomeric ring 106, wherein the central plane $P_1$ extends through a center C of the elastomeric ring 106 between the first circular-shaped edge 116(1) and the second circular-shaped edge 116(2). This is also because, in either position of the first or second pervious layer 118(1), 118(2) of the covering 112 disposed adjacent to a cervical os, bodily fluid can pass through either of the first or second pervious layer 118(1), 118(2) positioned adjacent to the cervical os to reach the absorbent pad 110 retained in the cavity 120 formed by the first and second pervious layers 118(1), 118(2). This allows for an easier use of the tampon 100. For example, if only one of the first and second pervious layers 118(1), 118(2) of the covering 112 were pervious, a user would have to understand which side of the covering 112 is pervious and then orient the tampon 110 with that pervious side positioned adjacent to the cervical os. In the exemplary tampon 100, the user does not have to understand which side of the tampon 100 has the pervious layer because both sides of the tampon 100 have respective first and second pervious layers 118(1), 118(2). The user can position the tampon 100 in the vaginal canal with either side positioned adjacent to the cervical os.

Also, with reference to the exemplary tampon 100 in FIGS. 1A and 1B, to further support the tampon 100 being bi-directionally positionable within a vaginal canal, the covering 112 of the tampon 100 is at least partially positioned between the first circular-shaped edge 116(1) and the second circular-shaped edge 116(2) of the elastomeric ring 106. In this manner, at least portions of the first and second circular-shaped edges 116(1), 116(2) of the elastomeric ring 106 will extend beyond respective outer surfaces 122(1), 122(2) of the first and second pervious layers 118(1), 118(2) of the covering 112 to form a respective collection chamber 124(1), 124(2) on each side of the elastomeric ring 106. The collection chambers 124(1), 124(2) are bounded by a portion of the inner surface 114 of the elastomeric ring 106 that extends beyond outer surfaces 122(1), 122(2) of the respective first and second pervious layers 118(1), 118(2). This may further aid in collection of bodily fluids within the area of the central aperture 108 of the elastomeric ring 106 that will then pass through either the first or second pervious layer 118(1), 118(2) (depending on the orientation of the tampon 100) of the covering 112 to reach the absorbent pad 110. Note however that the first and second pervious layers 118(1), 118(2) of the covering 120 may also have the ability to absorb bodily fluids as well.

Figures 3A, 3C:
FIGS. 3A and 3B are top and top perspective views, respectively, of the bi-directionally positionable tampon in FIGS. 1A and 1B in a deformed state.
FIG. 3C is a top view of the bi-directionally positionable tampon in FIGS. 1A and 1B in an unformed state.
Figure 3B:
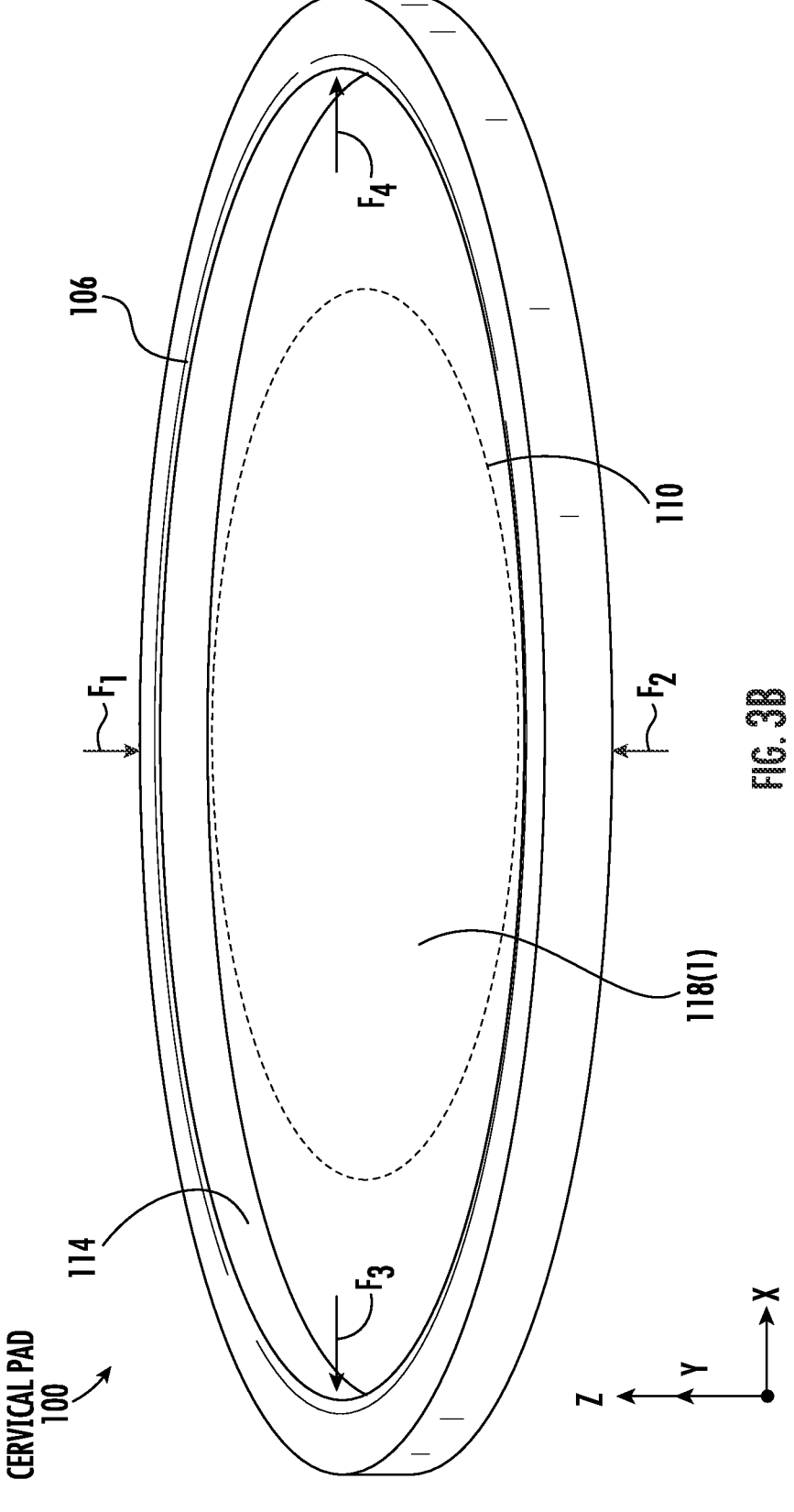

Also, in the example of the tampon 100 in FIGS. 1A and 1B, to prevent or reduce the tearing or compromising of the structural integrity of the absorbent pad 110 when the elastomeric ring 106 is deformed (like shown in FIGS. 3A and 3B) to insert the tampon 100 into a vaginal opening, the absorbent pad 110 is floatingly disposed in the cavity 120 between the first and second pervious layers 118(1), 118(2) of the covering 112. In other words, the absorbent pad 110 in this example is not fixedly attached to the first or second pervious layers 118(1), 118(2), but rather disposed in the cavity 120 that is formed by the first or second pervious layers 118(1), 118(2) being in a fixed position adjacent to each other within the elastomeric ring 106. The first and second pervious layers 118(1), 118(2) protect the absorbent pad 110. The absorbent pad 110 is floating in the cavity 120 unattached to either the first or second pervious layers 118(1), 118(2) and the elastomeric ring 106. In this manner, when the elastomeric ring 106 is deformed for insertion of the tampon 100 into a vaginal opening, such as by application of forces $F_1$, $F_2$ to the elastomeric ring 106 as shown in FIGS. 3A and 3B, resulting forces $F_3$, $F_4$ are applied outwardly to the elastomeric ring 106. These resulting forces $F_3$, $F_4$ are translated to the first and second pervious layers 118(1), 118(2) of the covering 112 attached to the elastomeric ring 106. However, such forces $F_3$, $F_4$ are not directly translated to the absorbent pad 110, because the absorbent pad 110 is floating between the first and second pervious layers 118(1), 118(2). But as discussed in examples below, the first and second pervious layers 118(1), 118(2) are chosen from a material(s) that allows the first and second pervious layers 118(1), 118(2) to stretch and absorb force imparted to them when the elastomeric ring 106 is bent with no or lower risk of tearing of the first and second pervious layers 118(1), 118(2). This allows the absorbent pad 110 to be chosen from a material(s) that is based on the desired collection and absorption properties without such properties having to be compromised to avoid or reduce tearing, advantage of the covering 112 in the tampon 100 is that it forms the cavity 120 to protect the absorbent pad 110 and prevent any contamination from the absorbent pad 110 (e.g., material flake off) into a vaginal canal in which the tampon 100 is inserted.

Note that while the tampon 100 in FIGS. 1A-3C shows an elastomeric ring 106 that is circular shaped, such is not limiting. The term "ring" does not imply and is not limited to a perfect circular shape or a substantially circular shape. For example, the elastomeric ring 106 could have also have degree of an ellipse/oval shape rather than circular shape. Such a shape may be desired, for example, if the material of the covering 112 does not have a stretch or extendability in all directions equally and/or without damage or is biased to certain directions. The shape of the elastomeric ring 106 could be designed so that the covering 112 is attached to the elastomeric ring 106 such that short diameter is positioned in a direction such that the covering 112 is less extendible. In this example, squeezing of the elastomeric ring 106 would have less distortion if the squeezing takes place along the narrower diameter of the elastomeric ring 106.

Also note that while the above description of the absorbent pad 110 of the tampon 100 being floatingly disposed in the cavity 120 between the first and second pervious layers 118(1), 118(2) can prevent or reduce tearing of the absorbent pad 110 when force is applied to the elastomeric ring 106, the tampon 100 is not limited and does not preclude any tearing of the absorbent pad 110. For example, the absorbent pad 110 may be attached to the elastomeric ring 106 when the absorbent pad 110 is not floating during the manufacturing of the tampon 100 so that the absorbent pad 110 position is controlled. This could cause tearing during manufacture when the elastomeric ring 106 is handled or otherwise processed. Further, the absorbent pad 110 could be torn or its material stretched even when the elastomeric ring 106 is squeezed during use if tightly secured between the first and second pervious layers 118(1), 118(2) due to friction. Even so, the absorbent pad 110 can remain completely useful for absorbing fluids even after any such tear, because it remains incased in the covering 112 and remains a viable absorbent.

Figures 4A, 4B:
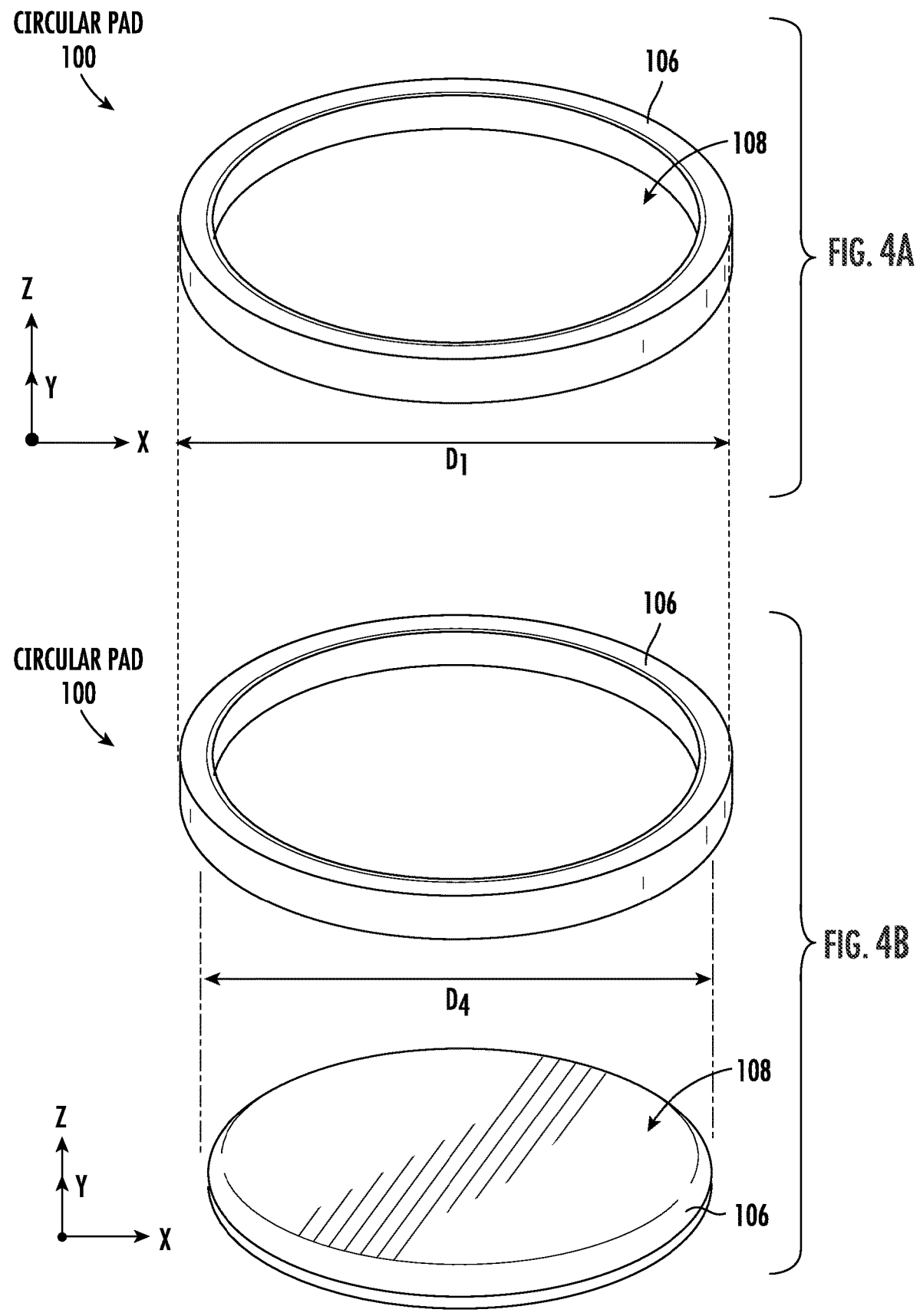
FIGS. 4A and 4B are top perspective views of the elastomeric ring of the bi-directionally positionable tampon in FIGS. 1A and 1B without the covering and absorbent pad installed.

FIGS. 4A and 4B are top perspective views of the elastomeric ring 106 of the tampon 100 in FIGS. 1A and 1B without the covering 106 and absorbent pad 110 installed in the elastomeric ring 106 to show and discuss additional exemplary details. As shown in FIGS. 4A and 4B, the elastomeric ring 106 comprises a circular-shaped ring. The elastomeric ring 106 can be made out of any material that is elastomeric or has an elastomeric property. The elastomeric ring 106 can be constructed as a soft, smooth, and/or colored polymeric material that is approved for internal or in vivo use as a Class II FDA device. The elastomeric ring 106 in this example is made as a single piece from a mold. The elastomeric ring 106 can be of sufficient hardness to easily be inserted and removed from a vaginal channel. For example, the durometer should be in the range of 75-80. The outer diameter $D_1$ of the elastomeric ring 106 is 2.5 inches in the example in FIGS. 4A and 4B. The cross-section height $H_1$ of the elastomeric ring 106 in the Z-axis direction is between 0.3 and 0.5 inches in one example as shown in FIG. 1B. In this manner, in this example, the elastomeric ring 106 is substantially reduced in width, shown as height $H_1$, versus its outer diameter $D_1$, or length, to be substantially flat or "horizontal" for convenient insertion and placement adjacent to a cervical os. The elastomeric ring 106 has a generally rectangular transverse cross-section in the X-axis direction as shown in FIGS. 1B and 3B whether bent or not. It may be desired for the transverse cross-section width $W_1$ of the elastomeric ring 106 as shown in FIG. 1B to be less than the transverse cross-section height $H_1$ so that it is easier to pinch or squeeze the elastomeric ring 106 for manipulation and insertion into a vaginal opening while elastomeric ring 106 will maintain a substantially flat configuration as shown in FIGS. 3A and 3B. The elastomeric ring 106 in this example is designed to collapse on itself on the sides in which the force is applied while elongating outward on the sides that force is not being applied as shown in FIGS. 3A and 3B. When viewed from the side as shown in FIG. 3B, the elastomeric ring 106 remains straight and has resistance to bending in the Z-axis direction. In this example, as shown in FIGS. 3A and 3B, the elastomeric ring 106 is configured to deform from a circular shape with the initial outer diameter $D_1$ to an oval shape with a deformed diameter $D_2$, with the deformed diameter $D_2$ of the oval shape being greater than the initial outer diameter $D_1$ of the circular shape of the elastomeric ring 106.

The covering 112 of the tampon 100 may be configured to be stretched up to 40% in any direction without the covering 112 tearing or with reduced tearing. The first and second pervious layers 118(1), 118(2) may be comprised of respective first and second fabric layers that are pervious to bodily fluids. For example, the first and second pervious layers 118(1), 118(2) may be comprised of cotton, including a woven, jersey knit cotton. The first and/or second pervious layers 118(1), 118(2) could also be comprised of a natural material or synthetic material, such as rayon, polyester, nylon, polyethylene, as examples. Such natural or synthetic material could be woven material, such as a knit, or non-woven material. An advantage of a knit is that it allows the cavity 120 to extend when pulled in different directions and then return to its non-extended, non-deformed state when the pulling force is removed. The first and second pervious layers 118(1), 118(2) may also include at least one of an extensible non-woven, polyolefin and an extensible non-woven, polyester. The cavity 120 that is formed between the first and second pervious layers 118(1), 118(2) for supporting the absorbent pad 110 may be defined by the first and second pervious layers 118(1), 118(2) and the inner surface 114 of the elastomeric ring 106. Alternatively, the cavity 120 that is formed between the first and second pervious layers 118(1), 118(2) may be defined fully or completely by the first and second pervious layers 118(1), 118(2), such portions outside of the area of the absorbent pad 110 between the first and second pervious layers 118(1), 118(2) are sewn or otherwise bonded to each other (e.g., by glue or mechanical bonding) in the central aperture 108 of the elastomeric ring 106 as opposed to only being secured to the inner surface 114. To further support the flow of fluid through the first and/or second pervious layers 118(1), 118(2), the first and/or second pervious layers 118(1), 118(2) may also be fenestrated. The first and second pervious layers 118(1), 118(2) could also be of the same size, and thus would also be of the same surface area, to provide a symmetrical shape and size of the first and second pervious layers 118(1), 118(2) as installed in the elastomeric ring 106 of the tampon 100.

As discussed above, the absorbent pad 110 is chosen from a material to absorb bodily fluids. The absorbent pad 110 can be designed to collect and hold vaginal fluid until such time that the tampon 100 is removed. For example, the absorbent pad 110 could be or include a cotton, including a non-woven, spunlaced cotton (e.g., 100% non-woven, spunlaced cotton). Spunlace cotton is not biaxially stretchable and the absorbent pad 110 retains its structure, so the cavity 120 formed by the covering 106 can protect a spunlace cotton absorbent pad 110. As discussed previously, the absorbent pad 110 can be left floating in the cavity 120 without being permanently attached, bonded, or otherwise tethered to the cavity 120 and/or the elastomeric ring 106. The absorbent pad 110 can be chosen from different materials and material combinations to achieve the desired absorbency volume. The absorbent pad 110 is designed to be floating in the cavity 120 formed by the first and second pervious layers 118(1), 118(2) of the covering 102 as discussed above. This is so that the absorbent pad 110 can move within the cavity 120, for example, if the elastomeric ring 106 is pinched or squeezed. Thus, as shown in FIG. 3C, the diameter $D_3$ of the absorbent pad 110 can be less than the diameter $D_4$ of the central aperture 108 of the elastomeric ring 106. The size and/or diameter $D_3$ of the absorbent pad 110 that is retained in the cavity 120 formed by the covering 102 can also be adjusted based on the desired absorbency to be achieved.

It may be desirable to attach a covering, similar to covering 112, to an elastomeric ring to provide a tampon in other arrangements. For example, it may be desired to provide a method of attaching a covering to an elastomeric ring without a fixed attachment, such as glue for example. For example, an elastomeric ring may be designed to receive and secure an inserted covering with embedded absorbent pad without being fixed attached to the ring. In this manner, the elastomeric ring may be reusable, and the covering and integrated absorbent pad disposable.

Figure 5A:
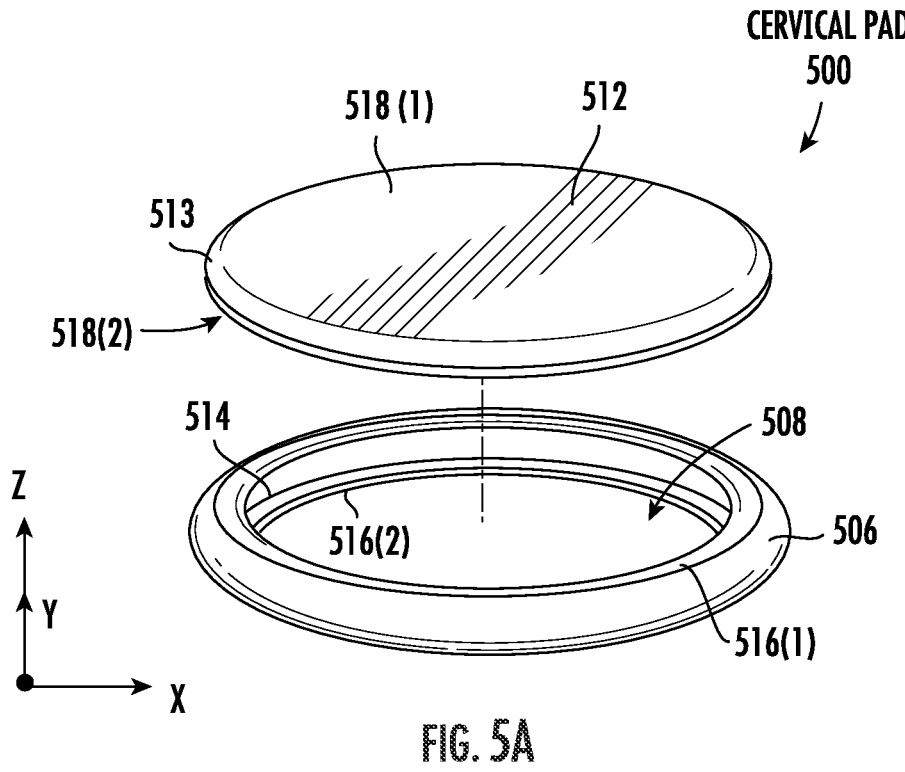
FIGS. 5A and 5B are top perspective views of another exemplary bi-directionally positionable tampon that has an absorbent pad disposed in a cavity formed between adjacent pervious fabric layers of a covering attached to an elastomeric ring.
Figure 5B:
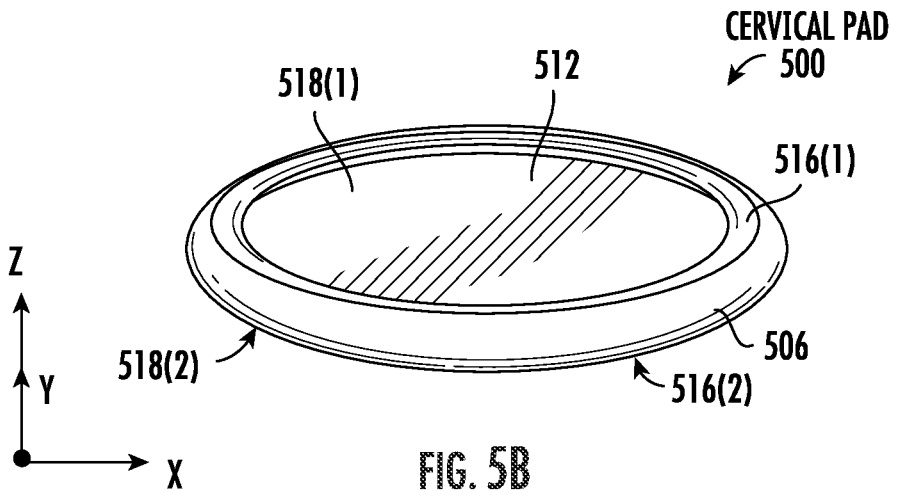

In this regard, FIGS. 5A and 5B are top perspective views of another exemplary bi-directionally positionable tampon 500 that has an alternative elastomeric ring 506. The elastomeric ring 506 defines a central aperture 508. The elastomeric ring 506 is substantially reduced in height versus its outer diameter or length to be substantially flat or "horizontal" for convenient insertion and placement adjacent to a cervical os. The profile and shape of the inner surface 514 of the elastomeric ring 506 is such that it is designed to receive a covering 512 with a complementary outer surface 513 that is designed to mate with the inner surface 514 of the elastomeric ring 506. The covering 512 can be made of first and second pervious layers 518(1), 518(2), similar to the first and second pervious layers 118(1), 118(2) of the tampon 100 in FIGS. 1A and 1B. The covering 512 houses an absorbent pad 510. By the first and second outer edges 516(1), 516(2) being disposed inward into the central aperture 508 of the elastomeric device, the first and second outer edges 516(1), 516(2) can retain an inserted covering 512 in the Z-axis direction like shown in FIG. 5B. The covering 512 can be squeezed and inserted between inner surfaces 514 of the elastomeric ring in the X- and Y-axis directions to be inserted inside the central aperture 508 with the outer surface 513 of the covering 512 being friction fit and adjacent to the inner surface 514 of the elastomeric ring 506 due to the resiliency of the covering 512 when no longer squeezed. The first and second outer edges 516(1), 516(2) also serve to retain the covering 512 in the central aperture 508 in the Z-axis direction. Then, to remove the covering 512, a force can be applied in the Z-axis direction to the covering 512 to reduce its length to disengage its outer surfaces 513 from the first and second outer edges 516(1), 516(2) and inner surface 514 of the elastomeric ring 506. In this manner, elastomeric ring 506 services as a releasable attachment for the covering 512 and without the need for a permanent attachment between the covering 512 and the elastomeric ring 506, including without limitation glue or overmolding. However, note that an overmolding could also be disposed over the entire elastomeric ring 506 and covering 512.

Note that while the tampon 500 in FIGS. 5A and 5B shows an elastomeric ring 506 that is circular shaped, such is not limiting. The term "ring" does not imply and is not limited to a perfect circular shape or a substantially circular shape. For example, the elastomeric ring 506 could have also have degree of an ellipse/oval shape rather than circular shape. Such a shape may be desired, for example, if the material of the covering 512 does not have a stretch or extendability in all directions equally and/or without damage or is biased to certain directions. The shape of the elastomeric ring 506 could be designed so that the covering 512 is attached to the elastomeric ring 506 such that the short diameter is positioned in a direction such that the covering 512 is less extendible. In this example, squeezing of the elastomeric ring 506 would have less distortion if the squeezing takes place along the narrower diameter of the elastomeric ring 506.

Also note that, while the above description of the absorbent pad 510 of the tampon 500 being floatingly disposed in the cavity between the first and second pervious layers 518(1), 518(2) can prevent or reduce tearing of the absorbent pad 510 when force is applied to the elastomeric ring 506, the tampon 500 is not limited and does not preclude any tearing of the absorbent pad 510. For example, the absorbent pad 510 may be attached to the elastomeric ring 506 when the absorbent pad 510 is not floating during the manufacturing of the tampon 500 so that the absorbent pad 510 position is controlled. This could cause tearing during manufacture when the elastomeric ring 506 is handled or otherwise processed. Further, the absorbent pad 510 could be torn or its material stretched even when the elastomeric ring 506 is squeezed in use if tightly secured between the first and second pervious layers 518(1), 518(2) due to friction. Even so, the absorbent pad 510 can remain completely useful for absorbing fluid even after any such tear, because it remains incased in the covering 512 and remains a viable absorbent.

The previously discussed features and details of the elastomeric ring 106 and its covering 112 and integrated absorbent pad 110 for the tampon 100 in FIGS. 1A-1B and 3A-4B can also be applied to the tampon 500 in FIGS. 5A and 5B.

Figures 6A, 6B:
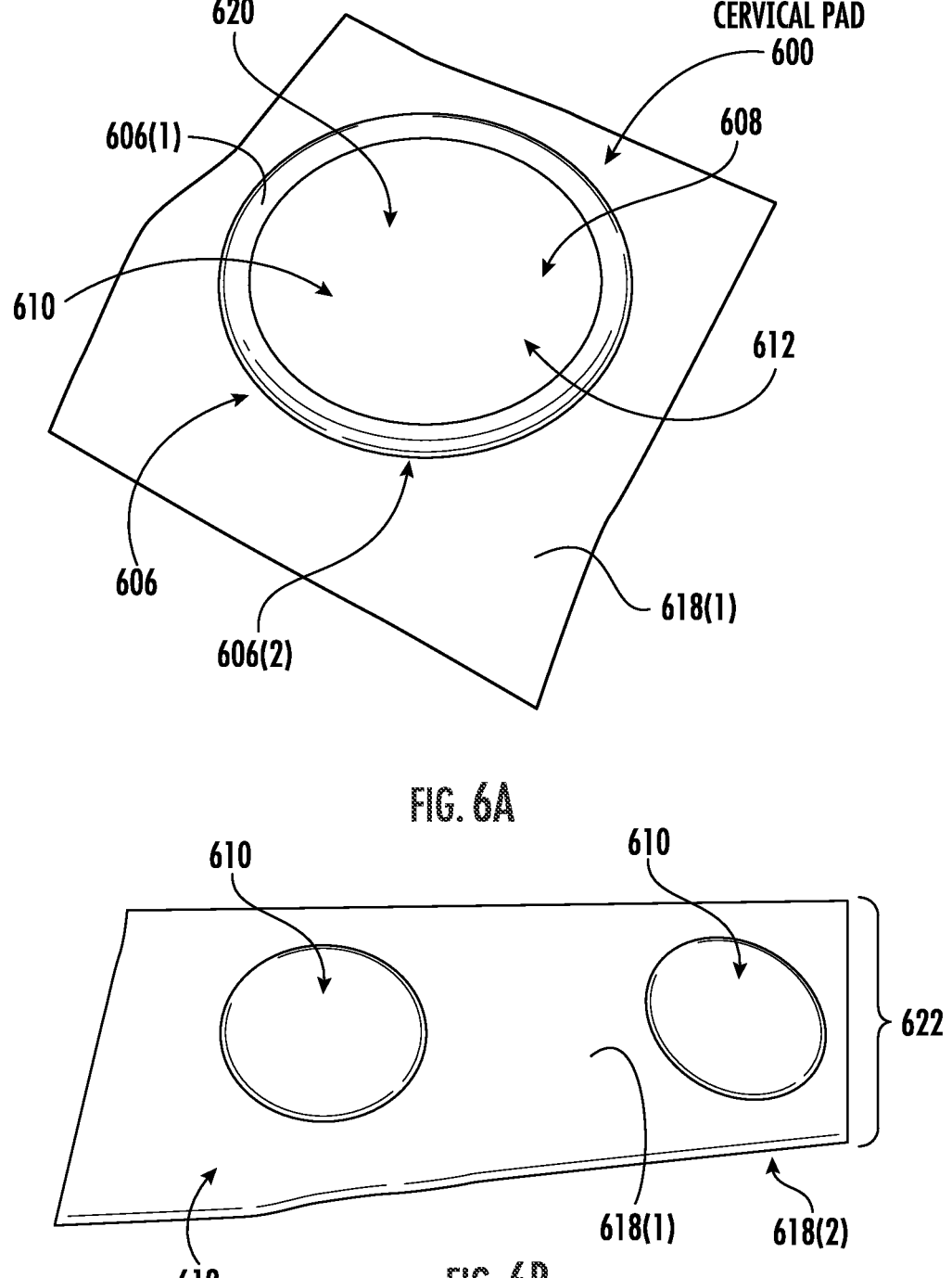
FIG. 6A is a top view of another exemplary bi-directionally positionable tampon that has an absorbent pad disposed in a cavity formed between adjacent pervious fabric layers of a covering compressed together by top and bottom portions of an elastomeric ring that form an elastomeric ring around the absorbent pad.
FIG. 6B is a top view of a material strip of first and second pervious fabric layers disposed adjacent to each other with multiple absorbent pads disposed between the fabric layers spaced apart and sewn into the fabric layers to prepare for top and bottom portions of respective elastomeric rings to be disposed around the absorbent pads to form multiple bi-directionally positionable tampons like shown in FIG. 6A.

FIG. 6A is a top perspective view of another exemplary bi-directionally positionable tampon 600 that has an absorbent pad 610 that is disposed in a cavity 620 formed between adjacent first and second pervious layers 618(1), 618(2) of a covering 612. In this example, the covering 612 is disposed between two half ring portions 606(1), 606(2) of an elastomeric ring 606 compressed together on respective sides of the first and second pervious layers 618(1), 618(2). This may be an easier method and easier in manufacture to dispose the covering 612 in the central aperture 608 to be supported by the elastomeric ring 606 than in the tampon 100 in FIGS. 1A and 1B. The elastomeric ring 606 is substantially reduced in height versus its outer diameter or length to be substantially flat or "horizontal" for convenient insertion and placement adjacent to a cervical os. However, the tampon 600 in FIG. 6A is disposable, meaning that the covering 612 is compressed and bonded between the adjacent half ring portions 606(1), 606(2) of the elastomeric ring 606. For example, the half ring portions 606(1), 606(2) of the elastomeric ring 606 is glued or otherwise bonded to a respective first and second pervious layer 618(1), 618(2) of the tampon 600. As shown in FIG. 6B, by providing the elastomeric ring 606 as two half ring portions 606(1), 606(2) that compress towards each other with the covering 612 disposed therebetween, this may allow coverings 612 with integrated absorbent pads 610 to be fabricated in a strip 622 like shown in FIG. 6B. Absorbent pads 610 can be disposed in a row between first and second pervious layers 618(1), 618(2). The strip 622 can then be put in a machine or other device that progresses the strip to allow half ring portions 606(1), 606(2) of an elastomeric ring 606 to be disposed on each side of the respective strip 622 on the respective first and second pervious layers 618(1), 618(2) and surrounding the absorbent pad 610 to form a tampon 600. The tampons 600 formed from the strip 622 can then be individually diced and the excess material from the first and second pervious layers 618(1), 618(2) outside the elastomeric rings 606 can be trimmed.

Note that while the tampon 600 in FIGS. 6A and 6B shows an elastomeric ring 606 that is circular shaped, such is not limiting. The term "ring" does not imply and is not limited to a perfect circular shape or a substantially circular shape. For example, the elastomeric ring 606 could have also have degree of an ellipse/oval shape rather than circular shape. Such a shape may be desired, for example, if the material of the covering 612 does not have a stretch or extendability in all directions equally and/or without damage or is biased to certain directions. The shape of the elastomeric ring 606 could be designed so that the covering 612 is attached to the elastomeric ring 606 such that the short diameter is positioned in a direction such that the covering 612 is less extendible. In this example, squeezing of the elastomeric ring 606 would have less distortion if the squeezing takes place along the narrower diameter of the elastomeric ring 606.

Also note that while the above description of the absorbent pad 610 of the tampon 600 being floatingly disposed in the cavity between the first and second pervious layers 618(1), 618(2) can prevent or reduce tearing of the absorbent pad 610 when force is applied to the elastomeric ring 606, the tampon 600 is not limited and does not preclude any tearing of the absorbent pad 610. For example, the absorbent pad 610 may be attached to the elastomeric ring 606 when the absorbent pad 610 is not floating during the manufacturing of the tampon 600 so that the absorbent pad 610 position is controlled. This could cause tearing during manufacture when the elastomeric ring 606 is handled or otherwise processed. Further, the absorbent pad 610 could be torn or its material stretched even when the elastomeric ring 606 is squeezed in use if tightly secured between the first and second pervious layers 618(1), 618(2) due to friction. Even so, the absorbent pad 610 can remain completely useful for absorbing fluid even after any such tear, because it remains incased in the covering 612 and remains a viable absorbent.

The previously discussed features and details of the elastomeric ring 106 and its covering 112 and integrated absorbent pad 110 for the tampon 100 in FIGS. 1A-1B and 3A-4B can also be applied to the tampon 600 in FIGS. 6A and 6B.

Figure 7A:
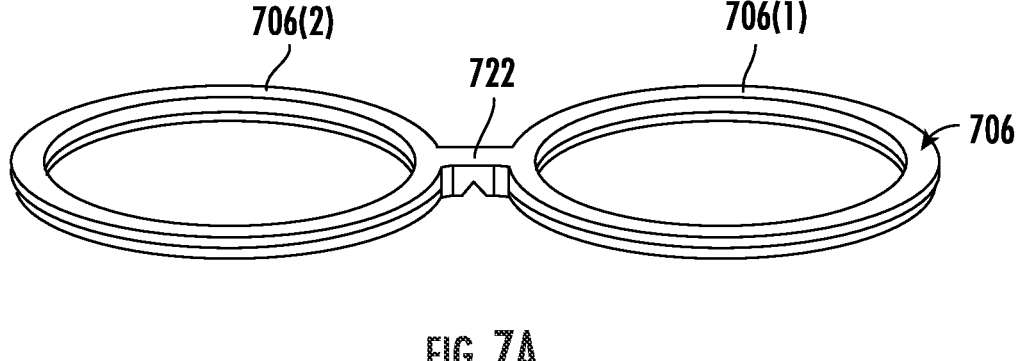
FIG. 7A is a top perspective view of another exemplary bi-directionally positionable clam-shell style elastomeric ring in an open position, configured to receive and support a covering that has an integrated absorbent pad disposed in a cavity formed between adjacent pervious fabric layers.
Figure 7B:
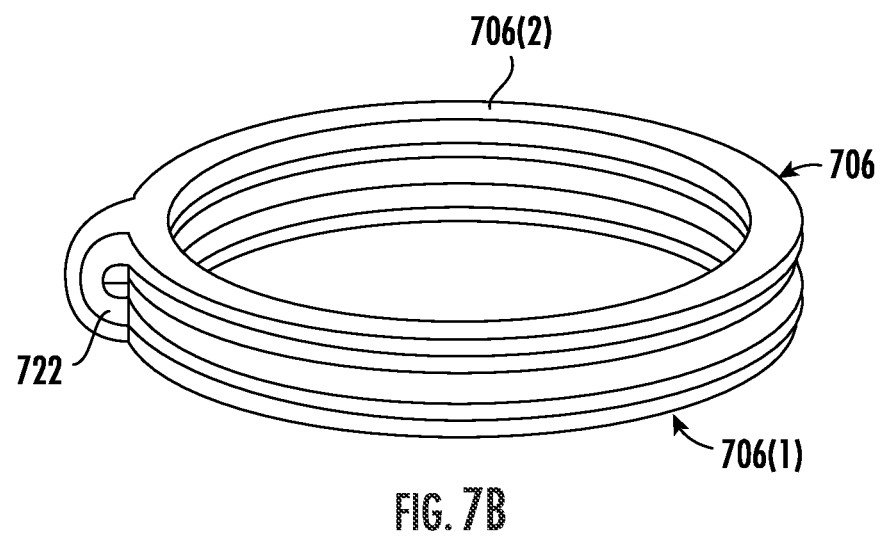
FIG. 7B is a top perspective view of the clam-shell style elastomeric ring in FIG. 7A in a closed position.

FIGS. 7A and 7B are a top perspective view of another exemplary elastomeric ring 706 that can be used to form a tampon that has an absorbent pad. The elastomeric ring 706 can be used to support a covering and integrated absorbent pad, like the covering 612 and absorbent pad 610 in FIGS. 6A and 6B. In this example, the elastomeric ring 706 is provided in the form of a clam-shell style arrangement, where the elastomeric ring 706 has a first half ring portion 706(1) that is attached to a second half ring portion 706(2) by a hinge 722. For example, the hinge 722 may be a living hinge where the hinge is formed in the elastomeric ring 706 as a single device, such as made from a single mold. A covering 612 in FIG. 6B can be disposed between two half ring portions 706(1), 706(2) of the elastomeric ring 706, with the half ring portion 706(1) being rotated and closed on the half ring portion 706(2), as shown in FIG. 7B, thus securing the covering 612 between the half ring portions 706(1), 706(2). As shown in FIG. 7B, by providing the elastomeric ring 706 as two half ring portions 706(1), 706(2) that compress on each other with the covering 612 disposed therebetween, this may allow coverings 612 with integrated absorbent pads 610 that are fabricated in the strip 622 in FIG. 6B to be placed on an assembly line and inserted and compressed in respective elastomeric rings 706. Like the elastomeric ring 506 in FIGS. 5A and 5B, the elastomeric ring 706 in FIGS. 7A and 7B can be reusable, wherein the two half ring portions 706(1), 706(2) are opened from each other and the inserted covering 612 removed and a new covering 612 inserted and the two half ring portions 706(1), 706(2) then closed on each other.

Note that while the tampon 700 in FIGS. 7A and 7B shows an elastomeric ring 706 that is circular shaped, such is not limiting. The term "ring" does not imply and is not limited to a perfect circular shape or a substantially circular shape. For example, the elastomeric ring 706 could have also have degree of an ellipse/oval shape rather than circular shape. Such a shape may be desired, for example, if the material of the covering 612 does not have a stretch or extendability in all directions equally and/or without damage or is biased to certain directions. The shape of the elastomeric ring 706 could be designed so that the covering 612 is attached to the elastomeric ring 706 such that the short diameter is positioned in a direction such that the covering 612 is less extendible. In this example, squeezing of the elastomeric ring 706 would have less distortion if the squeezing takes place along the narrower diameter of the elastomeric ring 706.

Also note that, while the above description of the absorbent pad 610 of the tampon 700 being floatingly disposed in the cavity between the first and second pervious layers 618(1), 618(2) can prevent or reduce tearing of the absorbent pad 610 when force is applied to the elastomeric ring 706, the tampon 700 is not limited and does not preclude any tearing of the absorbent pad 610. For example, the absorbent pad 610 may be attached to the elastomeric ring 706 when the absorbent pad 610 is not floating during the manufacturing of the tampon 700 so that the absorbent pad 610 position is controlled. This could cause tearing during manufacture when the elastomeric ring 706 is handled or otherwise processed. Further, the absorbent pad 610 could be torn or its material stretched even when the elastomeric ring 706 is squeezed in use if tightly secured between the first and second pervious layers 618(1), 618(2) due to friction. Even so, the absorbent pad 610 can remain completely useful for absorbing fluid even after any such tear, because it remains incased in the covering 612 and remains a viable absorbent.

The previously discussed features and details of the elastomeric ring 106 and its covering 112 and integrated absorbent pad 110 for the tampon 100 in FIGS. 1A-1B and 3A-4B can also be applied to the tampon 700 in FIGS. 7A and 7B.

It is also noted that the operational steps described in any of the exemplary aspects herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary aspects may be combined. It is to be understood that the operational steps illustrated in the flowchart diagrams may be subject to numerous different modifications as will be readily apparent to one of skill in the art.

The previous description of the disclosure is provided to enable any person skilled in the art to make or use the disclosure. Various modifications to the disclosure will be readily apparent to those skilled in the art, and the generic principles defined herein may be applied to other variations. Thus, the disclosure is not intended to be limited to the examples and designs described herein, but is to be accorded the widest scope consistent with the principles and novel features disclosed herein.

What is claimed is:

1. A tampon, comprising:

an elastomeric ring comprising an inner surface, an outer surface, a first circular-shaped edge, and a second circular-shaped edge opposite the first circular-shaped edge, wherein the inner surface defines a central aperture;

a covering attached to the elastomeric ring along the inner surface, the covering positioned within the central aperture with an entirety of the covering positioned between the first circular-shaped edge and the second circular-shaped edge, the covering comprising a first pervious layer and a second pervious layer at least partially defining a cavity therebetween, the first pervious layer and the second pervious layer being of a substantially same surface area, the first pervious layer comprising a first pervious material and the second pervious layer comprising a second pervious material; and an absorbent pad floatingly positioned within the cavity and substantially centered between the first circular-shaped edge and the second circular-shaped edge;

wherein a first portion of the inner surface extends beyond the first pervious layer to the first circular-shaped edge to define a first collection chamber bounded by the first portion of the inner surface and the first pervious layer; and wherein a second portion of the inner surface extends beyond the second pervious layer to the second circular-shaped edge to define a second collection chamber bounded by the second portion of the inner surface and the second pervious layer.

2. The tampon of claim 1, wherein the tampon is symmetrical about a central plane perpendicular to a central axis defined by the elastomeric ring, the central plane extending through a center of the elastomeric ring between the first circular-shaped edge and the second circular-shaped edge.

3. The tampon of claim 1, wherein the covering is configured to be stretched up to 40% in any direction without the covering tearing.

4. The tampon of claim 1, wherein the first pervious material comprises a first fabric material, and the second pervious material comprises a second fabric material.

5. The tampon of claim 4, wherein each of the first pervious material and the second pervious material comprises a woven, jersey knit cotton.

6. The tampon of claim 1, wherein each of the first pervious material and the second pervious material comprises at least one of:

an extensible, non-woven polyolefin; and an extensible, non-woven polyester.

7. The tampon of claim 1, wherein the first pervious layer and the second pervious layer completely define the cavity therebetween, with annular portions of the first pervious layer and the second pervious layer being sewn or otherwise bonded to one another around the cavity.

8. The tampon of claim 1, wherein each of the first pervious material and the second pervious material are configured to allow passage of vaginal discharge.

9. The tampon of claim 1, wherein the first pervious layer and the second pervious layer are fenestrated.

10. The tampon of claim 1, wherein the covering is attached to the inner surface of the elastomeric ring midway between the first circular-shaped edge and the second circular-shaped edge.

11. The tampon of claim 1, wherein the first pervious layer and the second pervious layer are a same size.

12. The tampon of claim 1, wherein the elastomeric ring is configured to span a vaginal opening adjacent to a cervical os.

13. The tampon of claim 1, wherein the elastomeric ring comprises a circular-shaped elastomeric ring.

14. The tampon of claim 1, wherein the elastomeric ring has a generally rectangular transverse cross-section such that a height of the transverse cross-section is greater than a width of the transverse cross-section.

15. The tampon of claim 1, wherein the elastomeric ring is configured to deform from a circular shape with an initial diameter to an oval shape, wherein a longest diameter of the oval shape is greater than the initial diameter of the circular shape.

16. The tampon of claim 1, wherein the covering is attached to the elastomeric ring by a permanent attachment.

17. The tampon of claim 16, wherein the permanent attachment comprises overmolding.

18. The tampon of claim 1, wherein the covering is attached to the elastomeric ring by a releasable attachment.

19. The tampon of claim 18, wherein the releasable attachment comprises a clam-shell.

20. The tampon of claim 1, wherein the absorbent pad is configured to absorb vaginal discharge.

21. The tampon of claim 1, wherein the absorbent pad comprises non-woven, spunlaced cotton.

22. The tampon of claim 1, wherein the absorbent pad has a smaller diameter than the central aperture.

23. The tampon of claim 1, being devoid of glue.

24. The tampon of claim 1, wherein the first pervious layer, the second pervious layer, and the absorbent pad are generally planar.

25. The tampon of claim 1, wherein the first collection chamber and the second collection chamber are on opposing sides of the absorbent pad such that the tampon may be used bi-directionally.

* * * * *